(12) United States Patent
Bel Rhlid et al.

(10) Patent No.: US 6,432,459 B1
(45) Date of Patent: Aug. 13, 2002

(54) PROCESS FOR THE PREPARATION OF FLAVORING COMPOSITIONS AND USE OF THESE COMPOSITIONS IN BAKERY PRODUCTS

(75) Inventors: Rachid Bel Rhlid, Epalinges; Imre Blank, Savigny, both of (CH); Christel Gunilla Steen, Raa (SE)

(73) Assignee: Nestec S.A., Vevey (SE)

( * ) Notice: Subject to any disclaimer, the term of this patent is extended or adjusted under 35 U.S.C. 154(b) by 0 days.

(21) Appl. No.: 09/582,323

(22) PCT Filed: Dec. 14, 1998

(86) PCT No.: PCT/IB98/02002

§ 371 (c)(1), (2), (4) Date: Aug. 10, 2000

(87) PCT Pub. No.: WO99/33358

PCT Pub. Date: Jul. 8, 1999

(30) Foreign Application Priority Data

Dec. 23, 1997 (EP) .............................................. 97122715

(51) Int. Cl.[7] .................................................. A23L 1/23
(52) U.S. Cl. ........................... 426/62; 426/61; 426/534; 426/535; 426/650
(58) Field of Search ............................... 426/534, 535, 426/61, 62, 650

(56) References Cited

U.S. PATENT DOCUMENTS 3,678,064 A    7/1972    Copier et al.

FOREIGN PATENT DOCUMENTS

EP    0486822 A1    5/1992

OTHER PUBLICATIONS

T. Hofmann et al., "Studies on the Formation and Stability of the Roast–Flavor Compound 2–Acetyl–2thiazoline," J. Agric. Food Chem., 1995, vol. 43, No. 11, pp. 2946–2950.

C.H. Td. Tonsbeek et al., "Components Contributing to Beef Flavor Isolation of 2–Acetyl–2–thiazoline from Beef Broth," J. Agr. Food Chem., vol. 19, No. 5, 1971, pp. 1014–1016.

Deutsche Forschungsanstalt für Lebensmittelchemie "Annual report 1997", XP–002066339, May 25, 1998.

Petra Münch et al., "Comparison of Key Odorants Generated by Thermal Treatment of Commercial and Self–Prepared Yeast Extracts: Influence of the Amino Acid Composition on Odorant Formation," J. Agric. Food Chem., 1997, vol. 45, No. 4, pp. 1338–1344.

*Primary Examiner*—Leslie Wong
(74) *Attorney, Agent, or Firm*—Young & Thompson

(57) ABSTRACT

A process for the preparation of a flavoring composition containing 2-acetyl-2-thiazoline (2-AT) and precursors thereof, as well as other flavor ingredients, which includes the bioconversion of a sulfur containing compound and an organic acid or derivative thereof in presence of a yeast, separating and recovering the supernatant of the reaction mixture. The flavoring composition obtained can be used especially for enhancing the roasty notes of bakery products.

18 Claims, No Drawings

PROCESS FOR THE PREPARATION OF FLAVORING COMPOSITIONS AND USE OF THESE COMPOSITIONS IN BAKERY PRODUCTS

CROSS REFERENCE TO RELATED APPLICATION

This is the 35 USC 371 national stage of International application PCT/IB98/02002 filed on Dec. 14, 1998, which designated the United States of America.

FIELD OF THE INVENTION

The present invention relates to a process for the preparation of flavouring compositions, more particularly the biogeneration of mixtures containing heterocyclic compounds and having roasty, popcorn-like or bread crust-like notes, and which are usable in foodstuffs, especially in bakery food products.

BACKGROUND OF THE INVENTION

Heterocyclic compounds are important known flavor constituents in many foods, such as meat and bread. Among these compounds, thiazoles and their derivatives play a key role in roasted flavors.

One of these thiazole derivatives with intense roasty flavor is 2-acetyl-2-thiazoline (2-AT), which was reported first as a volatile constituent of beef broth (see J. Agr. Food Chem. vol. 19, No 5, p. 1014–16, 1971). However, this compound has never been identified in bread or bakery products.

Various methods are already known to prepare 2-AT or similar thiazole compounds by organic synthesis (Recueil, vol. 91, p. 711–28, 1972) or through the Maillard reaction (J. Agr. Food Chem. vol. 43, No 11, p. 2946–50, 1995), which are however not appropriate for obtaining food-grade products.

SUMMARY OF THE INVENTION

Therefore, the main purpose of this invention was to provide a new and natural route for obtaining complex mixtures containing heterocyclic compounds, especially thiazole derivatives and more particularly 2-AT and precursors thereof, as well as other flavor ingredients.

A first object of the present invention is thus a process for the preparation of a flavouring composition containing 2-acetyl-2-thiazoline (2-AT), precursors thereof and other odorants, which comprises the bioconversion of a sulfur containing compound and an organic acid or a derivative thereof in presence of a yeast. The reaction mixture can advantageously be then submitted to a separation step, for example by centrifugation, so as to recover the supernatant from the mycelium, this supernatant being usable as a flavouring composition either directly in liquid form or after drying in powder form obtained by mild dehydration methods.

The sulfur-containing compound can be selected from the group comprising the compounds having the following formula (I):

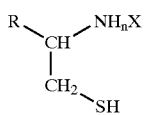

(I)

where

R is H, —COOH, —COOM (M=Na or K), —COONH$_4$, or —CO—NH—CH$_2$—COOH,

X is H, HCl, HBr or —CO—(CH$_2$)$_2$—CH(NH$_2$)—COOH, and n is 1 or 2, as well as peptides including said compounds of formula (I).

Among these compounds, those preferred are cysteamine and cysteine, or the salts and derivatives thereof, as well as glutathione.

As organic acids, those being of food grade such as the hydroxy- or keto-propionic acids, as well as their derivates, esters and salts thereof, can be used, for example lactic or pyruvic acids, or esters thereof such as ethyl-lactate or ethyl-pyruvate.

The preferred yeast used for the bioconversion is baker's yeast, for example in the form of a powder, an extract or a cream solution, but other kinds of microorganisms can also be used, such as for example Candida versatilis, Debaromyces hansenii, Saccharomyces bayanus, etc. Preferably, the yeast is fresh, up to about 8 days, advantageously up to about 4 days, and kept in the refrigerator.

Regarding the respective quantities of the two starting products, they can be such as the molar ratio between the sulfur-containing compounds and the organic acid is about 1:1 or up to about 1:2. The concentration of these substrates in the reaction medium can be of 1 to 100 mMol, preferably from 10 to 30 mMol.

Generally, the yeast cream solution is used as from 20 to 60 ml per mMol of substrate, but this range can be adjusted according to the yeast and the substrates concerned.

Furthermore, the incubation with yeast can be carried out in presence of a sugar, such as tetroses, pentoses, hexoses, preferably glucose.

Regarding the other reaction conditions, the incubation with the microorganisms is preferably carried out in the activation conditions of the carboxypeptidase enzyme. This can be under aerobic or anaerobic conditions, preferably aerobic during 2 to 72 hr, preferably 4 to 48 hr, and at a pH of 7.0 to 11.0, preferably 8.0 to 10.0. The temperature of the reaction can be of 20 to 50° C., preferably 30–40° C., and it can be carried out under medium to high agitation conditions.

The reaction medium can be water or a buffer solution, such as phosphate or carbonate-bicarbonate.

As already mentioned, the reaction mixture is advantageously after bioconversion submitted to a separation step, preferably by centrifugation, so as to recover the supernatant from the mycelium. The supernatant can be either maintained as it is in liquid form or converted into a powder using mild conditions, e.g. by spray or freeze drying (with or without maltodextrin, cyclodextrin, modified starch, etc.).

The flavouring composition thus obtained by the process according to the invention revealed a flavour described after sensory evaluation as roasty, meaty, sausage-like, dried sausage-like and somewhat amine-like.

The supernatant obtained by the process according to the invention may also be dried in a vacuum oven at a temperature between 40 and 80° C. during 2 to 5 hours, preferably 3 to 4 hours, in order to provide a powder having a more pronounced roasty, popcorn-like and bread crust-like notes.

It has been further suprinsingly found that when the process according to the invention comprises a subsequent step of heat treatment of the flavouring composition obtained, which constitutes another object of the present invention, said composition is transformed into another flavouring composition, which is presenting a different flavour, i.e. with more pronounced roasty, popcorn-like or breadcrust-like notes, and to a lesser extent meaty-like note.

This can be explained by the fact that, under the action of the heating, the concentration of 2-AT is significantly increased (about 10 to 100 times) and that other compounds such as 2-methylthiazolidine, N-acetylcysteamine, 2-methyl-3-furanthiol and 3-mercapto-2-pentanone are fully or at least partially decomposed.

The additional heat treatment can be carried out either directly on the liquid composition as recovered after the bioconversion process, or on the dehydrated powder prepared from said liquid composition, if appropriate in presence of other ingredients.

The preferred conditions of this additional heat treatment, which have been experimentally determined, are the following : 100–250° C., 10 to 120 min, and pH comprised between 6 and 10, preferably between 7 and 8.

Also surprisingly, it has been further shown that a flavouring composition presenting such an increased content of 2-AT can advantageously be used in foodstuffs and more particularly in bakery products, so as to improve the roasty, popcorn-like and bread crust-like notes thereof; this constitutes still another object of the present invention.

Furthermore, in the case of the bakery products, the original flavouring composition before heat treatment can be either added to the various constituents and ingredients to be baked (in dough) or applied as a coating for example by pulverizing the liquid composition or spreading the powder form thereof on the prebaked products.

DETAILED DESCRIPTION OF THE INVENTION

The present invention will now be illustrated by reference to the following Examples.

EXAMPLE 1

Preparation of Flavouring Composition A

One liter of commercial yeast cream (from Hefe Schweiz AG) was centrifuged for 15 min at 5000 rpm, and the supernatant was discarded. The mycelium was resuspended in 1 liter of 0.2 M sodium bicarbonate-sodium carbonate buffer at pH 9.8. This yeast cream solution was then used for the bioconversion.

150 ml of this yeast cream solution were placed in a 500 ml flask equipped with an electrode and a magnetic stirrer (500 rpm). The flask was kept at 35° C. using an oil bath and the pH adjusted to 9.8 with 2M sodium hydroxide. The pH was automatically maintained throughout the reaction using a Metrohm pH-stat device. Cysteamine (385 mg, 5 mmol) and ethyl-L-lactate (590 mg, 5 mmol) were then added. Ten and 5 g of D-glucose were added after 4 and 24 h of incubation, respectively. After 48 hr of reaction, the mixture was centrifuged and the supernatant was recovered as Composition A. A part of this composition was then freeze-dried to composition AF.

EXAMPLE 2

Preparation of Flavouring Composition B with Enhanced Roasty Note

Thirty ml of the Composition A as liquid phase (supernatant) were acidified to pH 7 with 15% hydrochloric acid, and refluxed at 100° C. for 60 min in a 50 ml flask equipped with a reflux condenser and a magnetic stirrer to obtain a Composition B1. Another 30 ml of the same Composition A were refluxed without acidification (pH 10) to obtain a Composition B2. The reaction mixtures can be dried in the presence of a support such as maltodrextin, cyclodextrin, modified starches, etc.

EXAMPLE 3

Characterization of Compositions A and B

The main odorant compounds present in Compositions A and B obtained by the process according to the invention have been identified, and the flavour of said compositions have been evaluated, more particularly on diethyl-ether extracts of these compositions. For the extraction, 15 ml of the supernatant of each composition A, B1 and B2 were saturated with NaCl and extracted with purified diethyl-ether, using a liquid-liquid extractor (rotary perforator). The organic phase of Composition A was dried over anhydrous sodium sulfate and concentrated to about 1 ml by microdistillation. The organic phases of B1 and B2 were dried over anhydrous sodium sulfate, purified by high vacuum transfer at $3\times10^{-3}$ mbar, and concentrated to 1 ml.

A. Gas Chromatographic Analysis

About twenty odor-active volatile compounds were detected in the aroma extracts of the Compositions A, B1 and B2 by gaz chromatography-olfactometry (GC-O), using "Carlo Erba" gas chromatographs equipped with automatic cold oncolumn injector, flame ionization detector and sniffing port, and by gas chromatography-mass spectrometry (CG-MS) using a "Finnigan MAT-8430" apparatus.

Among these about twenty compounds, 2-AT was identified in the aroma extract of Composition A by GC-O and GC-MS, its sensory and chromatographic properties being identical to those of the reference compound. The concentration of 2-AT obtained was low, i.e. about 0.3 mg/kg of Composition A. Other thiazolines as well as other odorants were further identified, as reported in the following Table 1.

The analyses made on the aroma extracts of both Compositions B1 and B2 have shown that 2-AT became the dominant aroma compound, the amount of 2-AT being higher in B1 than in B2, thus indicating that a heat treatment at pH 7 is more favourable to the formation of 2-AT than at pH 10. The concentration of 2-AT obtained was of 12 mg/kg in Composition B2 and of 26 mg/kg in Composition B1.

The GC analyses have further shown that, apart the significant increase of 2-AT, other compounds were decomposed, such as MFT, N-acetylcysteamine and 3-mercapto-2-pentanone, whereas the amount of 2-methyl-thiazolidine sensibly decreased, as it can be seen in Table 1.

TABLE 1

Main odorants detected by GC/Olfactometry (CG/O) and GC-MS in the aroma extracts of Compositions B1 and B2 as compared to Composition A

| Compound | Identification | | | Aroma quality | Aroma Intensity | | |
|---|---|---|---|---|---|---|---|
| | RI | MS | Ref. | (GC-O) | Comp. A | Comp. B1 | Comp. B2 |
| Diacetyl | x | — | x | buttery, sweet | — | 2 | — |
| Isobutanol | x | x | x | malty | 2 | 1 | 1 |
| 3-Methyl-1-butanol | x | x | x | metallic, musty, malty | 2 | 2 | 1 |
| 2-Acetyl-1-pyrroline | x | — | x | roasty | — | 2 | 1 |
| Trimethylpyrazine | x | — | x | roasty, earthy | — | — | 2 |
| 2-Methylthiazolidine | x | x | x | amine-like, putrid | 3 | 1 | 2 |

TABLE 1-continued

Main odorants detected by GC/Olfactometry (CG/O) and GC-MS in the aroma extracts of Compositions B1 and B2 as compared to Composition A

| Compound | Identification | | | Aroma quality | Aroma Intensity | | |
|---|---|---|---|---|---|---|---|
| | RI | MS | Ref. | (GC-O) | Comp. A | Comp. B1 | Comp. B2 |
| 2-Ethyl-3,5-dimethyl-pyrazine | x | x | x | roasty, earthy | 2 | 2 | 2 |
| Isovaleric acid | x | x | x | sweaty, rancid | 2 | 1 | 1 |
| 2-Acetyl-2-thiazoline | x | x | x | roasty, popcorn | 2 | 3 | 3 |
| 2-Phenylethanol | x | x | x | spicy, almond-like | 1 | 1 | 2 |
| Furaneol | x | — | x | caramel-like | — | — | 2 |
| 2-Methyl-3-furanthiol | x | — | x | meaty, roasty | 2 | — | — |
| 3-Mercapto-2-pentanone | x | x | x | sulfury, catty | 2 | — | — |
| N-Acetylcysteamine | — | x | — | yeasty, musty | 2 | — | — |

RI: Retention Index; MS: Mass Spectrometry, Ref: Reference compound available; Aroma Intensity: 1 (weak), 2 (medium), 3 (high)

B. Sensory Evaluation

The aroma of each Composition A and Compositions B1 and B2 was evaluated by sniffing the headspace of the freshly prepared samples and of diethyl-ether extracts thereof. The assessors (generally 10) were asked to describe the aroma quality and intensity using sniffing strips.

The sensory evaluation made on Composition A resulted in a flavour described as roasty, meaty, amine-like (fishy), dried sausage and sausage-like of high intensity, which indicated that the roasty aroma of 2-AT was at least partly "covered" by other odorants.

On the contrary, the aroma qualities of both Compositions B1 and B2 were described as roasty, popcorn and bread crust-like showing high intensities, B1 being more intense than B2, which is in agreement with the above-reported gas chromatographic analysis.

EXAMPLE 4

Vacuum Drying of Composition A

Composition A was dried in a vacuum oven at different temperatures, i.e. 40–80° C. for 3.5 h. The resulting products (Composition AV) showed an intense roasty, popcorn-like note in powder form. High amounts of 2-AT were found in Composition AV (40° C.), i.e. 75 mg/kg, thus indicating that pronounced roasty notes can be obtained under mild conditions such as vacuum drying.

Composition AV (40° C.) was dissolved in hot water (1.5 g/100 ml). The aroma of the vacuum-dried product was described as intense roasty, popcorn-like.

EXAMPLE 5

Application to Bread Buns

A. Preparation of the bakery products A test bakery system was chosen for this Example. Wheat bread buns were used as model. The base recipe was as follows:

| | | |
|---|---|---|
| Wheat flour | 2000 g | (58.0%) |
| Water | 1100 g | (31.9%) |
| Yeast | 100 g | (2.9%) |
| Sugar | 80 g | (2.3%) |
| Skim milk powder | 80 g | (2.3%) |
| Shortening | 60 g | (1.7%) |
| Salt | 30 g | (0.9%) |
| Ascorbic acid | 0.4 g | (0.01%) |

The compositions tested were more particularly those described above and obtained before heat treatment (see Example 1) as A (liquid form) and AF (powder, freeze-dried), and the heat treatment step was therefore performed directly together with the bakery products to be produced.

These products were either added together with the rest of the ingredients ("in dough"), or as a coating on the top of the pre-baked buns ("on bun"). When added to the dough, the Composition A was mixed with the other ingredients together with the water, whereas the Composition AF was dissolved in the water. About 5 to 30 g of Composition AF, respectively 2 to 20 mg of Composition A, were added by batch.

When applied as a coating, both Composition A and AF were dissolved in water together with 4 g of Ultrasperse starch, and diluted up to 100 g; 1 g of the solution was applied on the top of the pre-baked buns.

Some of the ingredients were added without adjustment of the recipe, but whenever Composition A was added, the water in the base recipe was correspondingly reduced. Moreover, in the recipes with Composition AF, the flour was reduced by an equivalent to the dry matter content of said Composition AF.

More particularly, the dough was mixed in a Kemper mixer (1+2½ min.) and rolled out on a Rondo (3 kg of dough, 20 mn, 15 mm, turn 90°, 14 mm). It was then divided into several parts and rolled in a moulder. The buns were placed in aluminium moulds, fermented at 37° C. for 50 min, baked at 200° C. for 12 min., and cooled. For some of the products, a surface coating was applied after baking. The buns were then frozen in a blast freezer, packed in plastic bags, and stored at −25° C.

B. Sensory Screening Tests

The buns were then re-heated from the frozen state, either in a conventional baking oven at 200° C. for 15 minutes, or in microwave oven (750W, 1 min., rest for 1 min., 750 W, 1½ in., rest for 1½ min.). 5–6 products were tested on each occasion. An internal trained panel of 7–10 members participated in screening tests.

The results of these screening tests on buns with Composition A, and except for some of the products with said composition added in the dough, the overall aroma and flavour profiles of the buns have shown more pronouced total crust and crumb, as well as roasty aroma and flavour intensities.

The product with Composition AF applied as a coating on top of the pre-baked buns were all considered as acceptable, also from the apparence and texture point of view.

Better results have been obtained by re-heating the buns, for example in a conventional oven, which has given a higher total crust flavour intensity, mainly as a result of a more intense roasty crust flavour.

EXAMPLE 6

Application to Snacks

A. So-called Calzone Snacks were Produced Using the Following General Recipe for the Dough:

| | |
|---|---|
| Wheat Flour | 8917 g |
| Water | 4076 g |
| Margarine | 1274 g |
| Bakers Yeast | 382 g |
| Sugar | 191 g |
| Salt | 160 g |

The ingredients were mixed in a spiral mixer for 1 minute at low speed and 4 minutes at high speed. The dough was then fermented at room temperature for 30 minutes. The fermented dough was sheeted on a Fritsch sheeting line, and the dough thickness was reduced so that the weight of the individual Calzone pieces was 117 g, of which the filling conducted 65 g. The sheeted dough was divided into two equal parts of which one would serve as the bottom part of the Calzone and the other the upper part. Filling was placed on the bottom part and was then covered by the upper part. After punching, the Calzone pieces were fermented for 22 minutes in a proofing cabinet at 42° C. and 85% relative humidity. The Calzone pieces were then baked at 270° C. for 6.5 minutes, steaming 2×10 s in the very beginning of the baking. The products were then frozen.

The modified doughs were made in the same way by adding the flavouring ingredient AF, dissolved in part of the water, at the mixing stage, i.e. sample R (reference) and sample B using 0.5 g AF/100 g flour. The products were heated from the frozen state in a microwave oven at 750 W for 90 seconds.

B. Sensory Tests

The sensory panel consisting of 7–10 members evaluated aroma and flavour of the different Calzone products. During two training sessions, the panellists were presented to products with representative sensory characteristics. The descriptive tests were performed in duplicates, using a balanced, monadic serving. The samples were coded with three digit numbers. All panel sessions were conducted in booths equipped with air extraction and artificial daylight lightning. The panellists evaluated the samples for the intensity of the selected sensory attributes, using a five-degree discrete scale (none, weak, moderate, strong, very strong). The following descriptors were used: total aroma intensity, bread aroma, off-aroma, total flavour intensity, bread flavour, off-flavour, tomato flavour, spice flavour. Aroma was evaluated nasally, flavour in the mouth.

In general, the Calzone product was found to have a moderate bread aroma, a weak bread flavour, and moderate tomato and spice flavours. No off-aroma nor off-flavour was detected. The roasty bread-crust-like aroma and flavour was enhanced in product (B) compared to the reference sample (R). In addition, the pronounced tomato flavour perceived in the reference (R) was weaker in sample (B). The reason might be that the flavouring conceals the acid tomato flavour to a certain degree which means an additional improvement of the product quality.

EXAMPLE 7

Additional Thermal Treatment of the Flavouring Composition

In a 250 ml glass reactor with double jacket and stirrer, the following mixture was heated at 100° C. for 90 min.

| | |
|---|---|
| Liquid preparation Composition A | 100.00 g |
| Table salt | 60.00 g |

| | |
|---|---|
| di-Potassium phosphate | 5.00 g |
| Hydrochloric acid (32%) | 2.65 g |
| Palm Fat | 0.80 g |

After the reaction, 75 g of maltodextrine (Glucidex® 01) was added, and the mixture was dried in a vacuum oven at 75° C. for 3,5 h resulting in Compositon AH.

3,5 of the dried product (Composition AH) was dissolved in 250 ml of boiling water. A sweet, roasted note was preceived which was similar to the flavour of popcorn and bread crust.

The compositions obtained by the process according to the invention can thus advantageously be used to improve bread flavour, especilly by enhancing the roasty notes, more particularly refrigerated-baked and froze-baked products after reheating. They can also be applied for example to pizza and to other kinds of snacks, and any kind of bakery product.

We claim:

1. Process for the preparation of a flavoring composition containing 2-acetyl-2-thiazoline (2-AT) and precursors thereof, as well as other flavor ingredients, which comprises:
    reacting by bioconversion a sulfur-containing compound with an organic acid or derivative thereof, in the presence of a yeast as enzymatic catalyst to obtain a reaction mixture;
    separating the reaction mixture to obtain a supernatant; and
    recovering the supernatant of the reaction mixture.

2. The process according to claim 1, wherein the sulfur-containing compound is selected from the group comprising compounds of the following formula (I):

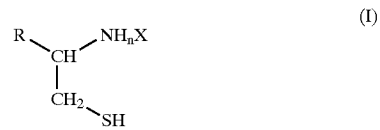

R is H, —COOH, —COOMe (Me=Na or K), —COONH$_4$, or —CO—NH—CH$_2$—COOH,

X is H, HCl, HBr or —CO—(CH$_2$)$_2$—CH(NH$_2$)—COOH, and n is 1 or 2, as well as peptides including such compounds of formula (I).

3. The process according to claim 1, wherein the sulfur-containing compound is cysteamine, cysteine, a salt or derivative thereof, or glutathione.

4. The process according to claim 1, wherein the organic acid is a food-grade organic acid.

5. The process according to claim 4, wherein the food-grade organic acid is a hydroxy- or ketopropionic acid, or a derivative thereof, a salt or an ester.

6. The process according to claim 4, wherein said acid is lactic or pyruvic acid, or an ester thereof.

7. The process according to claim 6, wherein the ester is ethyl-lactate or ethyl-pyruvate.

8. The process according to claim 1, wherein the yeast is baker's yeast in the form of a powder, an extract or a cream solution.

9. The process according to claim 1, wherein the molar ratio between the sulfur-containing compound and the organic acid is from 1:1 to 1:2.

10. The process according to claim 1, wherein the bioconversion is a fermentation reaction carried out in the presence of a sugar.

11. The process according to claim 10, wherein the sugar is selected from the group consisting of tetroses, pentoses, and hexoses.

12. The process according to claim 1, wherein the reaction is carried out in activation conditions of carboxypeptidase under aerobic or anaerobic conditions, during 2 to 72 hr, at a pH of 7.0 to 11.0, and at a temperature between 20 and 50° C.

13. The process according to claim 12, wherein the reaction is carried out in activation conditions of carboxypeptidase under aerobic or anaerobic conditions, during 4 to 48 hr, at a pH of 8.0 to 10.0, and at a temperature between 30 to 40° C.

14. The process according to claim 1, wherein the supernatant is dehydrated under mild conditions by freeze or spray drying, and recovered in the form of a powder.

15. The process according to claim 1, wherein the supernatant is dried under vacuum at a temperature of 40 to 80° C. and recovered in the form of a powder.

16. The process according to claim 1, further comprising subjecting the supernatant recovered from the reaction mixture to an additional heat treatment so as to increase the ratio of 2-AT to the precursors thereof.

17. The process according to claim 16, wherein the additional heat treatment is carried out at a temperature comprised between 100° C. and 250° C., during 10 to 120 min., and at a pH of 6 to 10.

18. The process according to claim 17, wherein the pH ranges from 7 to 8.

* * * * *